United States Patent [19]
McMahon

[11] Patent Number: 5,663,650
[45] Date of Patent: Sep. 2, 1997

[54] PORTABLE GRAIN MOISTURE METER

[75] Inventor: Mike McMahon, Salem, Ohio

[73] Assignee: Farmex, Inc., Aurora, Ohio

[21] Appl. No.: 510,000

[22] Filed: Aug. 1, 1995

Related U.S. Application Data

[62] Division of Ser. No. 220,885, Mar. 31, 1994, Pat. No. 5,493,229.

[51] Int. Cl.$^6$ ................................................. G01N 27/12
[52] U.S. Cl. ...................... 324/670; 324/664; 324/694; 324/721
[58] Field of Search ........................ 324/601, 664, 324/669, 670, 684, 685, 694, 720, 721

[56] References Cited

U.S. PATENT DOCUMENTS

| | | | |
|---|---|---|---|
| 3,068,404 | 12/1962 | Moore et al. | 324/721 X |
| 3,081,429 | 3/1963 | Moe | 324/670 X |
| 3,559,052 | 1/1971 | Fathauer | 324/670 X |
| 3,681,685 | 8/1972 | Tarry et al. | 324/670 X |
| 3,691,457 | 9/1972 | Kriellaars | 324/670 X |
| 3,743,930 | 7/1973 | Fathauer | 324/670 |
| 3,761,810 | 9/1973 | Fathauer | 324/670 |
| 3,794,911 | 2/1974 | Fathauer | 324/670 X |
| 4,044,607 | 8/1977 | Deal | 324/689 X |
| 4,147,976 | 4/1979 | Wang | 324/689 |
| 4,168,466 | 9/1979 | Boldt | 324/664 |
| 4,392,127 | 7/1983 | Steele | 324/696 X |
| 4,399,404 | 8/1983 | Resh | 324/670 X |
| 4,462,250 | 7/1984 | Stuart | 324/670 X |
| 4,584,522 | 4/1986 | Varela | 324/667 |
| 4,621,228 | 11/1986 | Toki et al. | 324/606 |
| 4,896,795 | 1/1990 | Ediger et al. | 324/664 X |
| 5,126,679 | 6/1992 | Spry | 324/696 |

*Primary Examiner*—Kenneth A. Wieder
*Assistant Examiner*—Glenn W. Brown

[57] ABSTRACT

A portable grain moisture meter has a large 16 character digital display allowing an alphabetical list of grain selections to be selectably displayed in full text format and subsequently tested for moisture content with the test results also displayed on the same display. The meter also has provisions for calibrating the meter to a remotely located meter and has dual temperature transducers for achieving automatic grain temperature compensation by monitoring both the grain temperature along with the cell temperature.

18 Claims, 12 Drawing Sheets

PORTABLE GRAIN MOISTURE METER

This is a division of application Ser. No. 08/220,885 filed Mar. 31, 1994 now U.S. Pat. No. 5,493,229.

BACKGROUND OF THE INVENTION

1. Field of the Invention

The present invention relates to grain moisture meter assemblies generally and particularly to portable grain moisture meters having back lit digital displays for indicating in full text the particular grain being tested and having inputs for calibrating the device to other meters as well as temperature compensation for the particular grain tested.

2. Description of the Prior Art

Portable grain testers utilizing the tested grain as a capacitance dielectric are known. Such devices utilize frequency attenuation through a constant volume of the dielectric as an indication of grain moisture. An example of such a device may be seen in U.S. Pat. Nos. 3,781,673 and 3,761,810. These devices in some cases even provided a limited digital display of the moisture content of the tested grain. However, these displays were limited to the moisture reading and did not provide a full text complementary digital readout of the particular grain being tested nor did they provide any biasing of the grain moisture readout to allow the operator to calibrate his device to the device that will measure the moisture content of the grain when it is transported, to the elevator for sale. Also, there was no back lighting of the digital readout to allow the operator to use his device inside areas of limited visibility or outside in either early morning light or dusk conditions.

Since grain moisture sensors test gain at various times of the season or even day, the grain tested may have a wide range of temperatures. Temperature measurement of the grain in the testing device is thus necessary to properly compensate for these differing grain temperatures. Prior art devices as found in U.S. Pat. No. 4,688,332 have such temperature measurement and compensation. These devices additionally sense even the air temperature to provide a check on the actual grain temperature. However, none of these devices compensate for the effect of the actual test cell of the grain measuring device. The test cell acts as an overpowering temperature sink to mask the temperature of the grain or at least make this measurement vary depending on the position of the measuring device in the test cell. Thus the test cell temperature needed to be also measured and taken into consideration.

In view of the foregoing it will be seen that the prior art portable grain measuring devices did not provide an easily viewed extensive full text digital display of not only the moisture content of the grain but an accompanying legend of the actual grain being tested along with other complementary inputs and information such as the biasing of the moisture readout as well as the amount of bias. Also, prior art devices failed to properly compensate for the temperature of the test cell itself in their temperature compensation circuits.

SUMMARY OF THE INVENTION

The present invention solves the problems associated with prior art devices as well as other problems by providing a capacitance type constant volume portable grain moisture meter that provides a large 16 character digital readout that is also back lit for easy visibility. The 16 character display allows the operator to alphabetically run through a series of spelled out, full text test grains before executing the test thereon. The display in addition to displaying in full text the selected grain also indicates the condition of the back light for the display being on or off by the presence or absence of a black dot.

The present invention also provides a biasing circuit which allows the grain testing meter to be calibrated to a remote grain testing center such as one located at the storage elevator where the grain will be sold and stored. Thus once the portable grain meter is calibrated to the meter of the grain elevator, the operator may be assured of testing the grain at the harvesting location and having certainty that when the harvested grain is delivered to the grain elevator for sale, the same moisture content will be measured there. Since a proper moisture content affects the sale price, this is a very important consideration for the grain harvester. The device also has a asterisk indicator on the digital display that indicates the measurement displayed is being biased to the remote location whenever such a bias is installed into the tester.

The accuracy of the grain measurement is assured by a dual temperature compensation circuit which has two temperature transducers for measuring both the grain temperature as well as the meter case or test cell temperature. The test cell acts as a thermal sink to the grain and the grain temperature will tend to drift toward equilibrium with the test cell with the grain closest to the cell walls being at near cell temperature while the grain in the center of the cell is at grain temperature. Thus the measurement of the grain temperature by itself is erroneous since the reading is dependent on the location of the temperature sensor within the grain sample. To eliminate this problem, the device of the present invention reads both the grain and cell temperatures by appropriate transducers with these readings being inputted to a microprocessor which mathematically calculates a differential temperature based on both of these readings. This differential temperature reading is then utilized in conjunction with a look up table for each individual grain tested and a compensating factor is used in the moisture measurement of the device.

In view of the foregoing it will be seen that one aspect of the present invention is to provide a portable grain moisture meter having a large digital display allowing the exhibiting of a full text detailed description of the grain to be tested.

Another aspect of the present invention is to provide a back lighted display for such a portable grain moisture meter allowing its operation in low light conditions of early morning light and dusk conditions.

Yet another aspect of the present invention is to provide a back lighted display on a portable grain moisture meter which will allow each grain variety to be easily calibrated to duplicate the readings of another remotely located grain meter such as one located at a local grain elevator.

Yet one more aspect of the present invention is to provide a portable grain moisture meter which will retain all its calibration data including remote location bias and last grain tested even if the unit is turned off or if the batteries should fail or are removed.

Still another aspect of the present invention is to provide a portable grain moisture meter whose measurements will not be affected by large temperature differences between grain temperatures and meter case temperatures.

These and other aspects of the present invention will be more fully understood from a review of the following detailed description of the preferred embodiment of the invention when considered in conjunction with the accompanying drawings.

DETAILED DESCRIPTION OF THE PREFERRED EMBODIMENT

Turning now to the drawing where the showings are intended to depict a preferred embodiment of the present inventions but not limit the invention thereto, FIGS. 1–6 show a portable grain moisture meter (10) having a front panel assembly (12) which includes a 16 character digital display panel (14) which is actuated to provide information regarding the grain testing procedure through a series of operator actuated switches depicted on a pressure sensitive membrane (16) of known construction and operation.

The moisture meter (10) is a capacitance type grain moisture meter utilizing a constant grain volume as the capacitance dielectric material whose frequency attenuation varies with moisture content of the dielectric and is thus able to measure the grain moisture thereby. The operation of such devices is described in prior art U.S. Pat. Nos. 3,761,810 and 3,781,673 the contents of which are incorporated herein by reference and the reader is referred thereto for a fuller explanation of the structure and operation of such devices.

Figure 3:
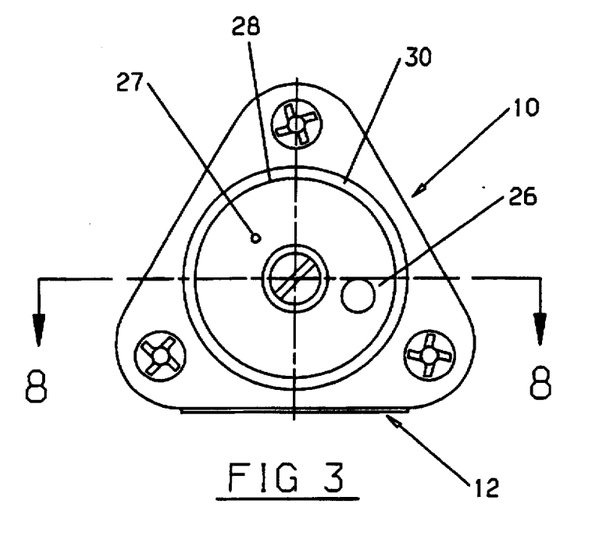
FIG. 3 is the FIG. 2 moisture meter showing the top cap removed to exhibit the grain compartment or test cell of the meter.
Figure 4:
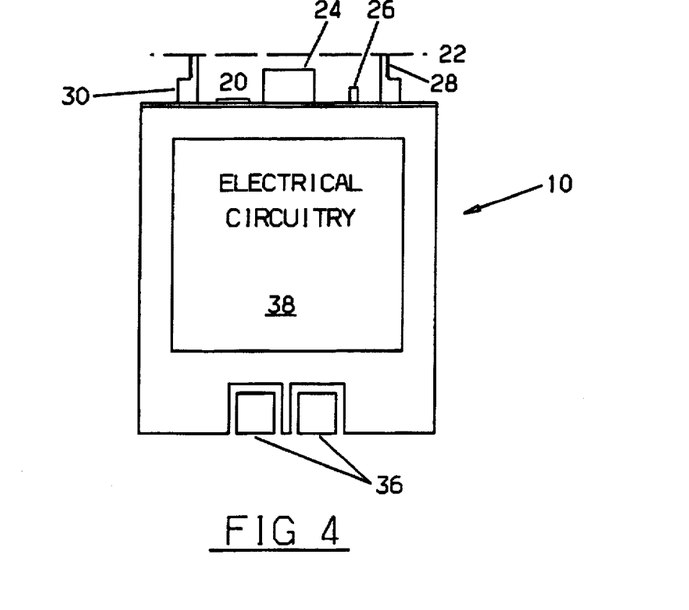
FIG. 4, is a cut away front view of the FIG. 1. moisture meter taken along section A—A as shown in FIG. 3.

In the meter (10) the constant grain volume is provided by unthreading a cap (18) to reveal a grain compartment (20) or test cell into which the grain to be tested is poured to an overflow level (22) around electrode (24) and grain temperature sensor (26) extending up into the grain compartment (20) forming the test cell. Inside this compartment (20) is also located a case temperature sensor (27) embedded in the floor of the test cell. The cap (18) has inside threads (21) which are complimentary to threads (28) found on the outside surface (30) of the grain compartment (20). The cap (18) also has an inside plate (19) which is approximately the diameter of the grain compartment to compresses the grain sample in the test cell to a predetermined compression as will be seen later.

Figures 1, 1A:
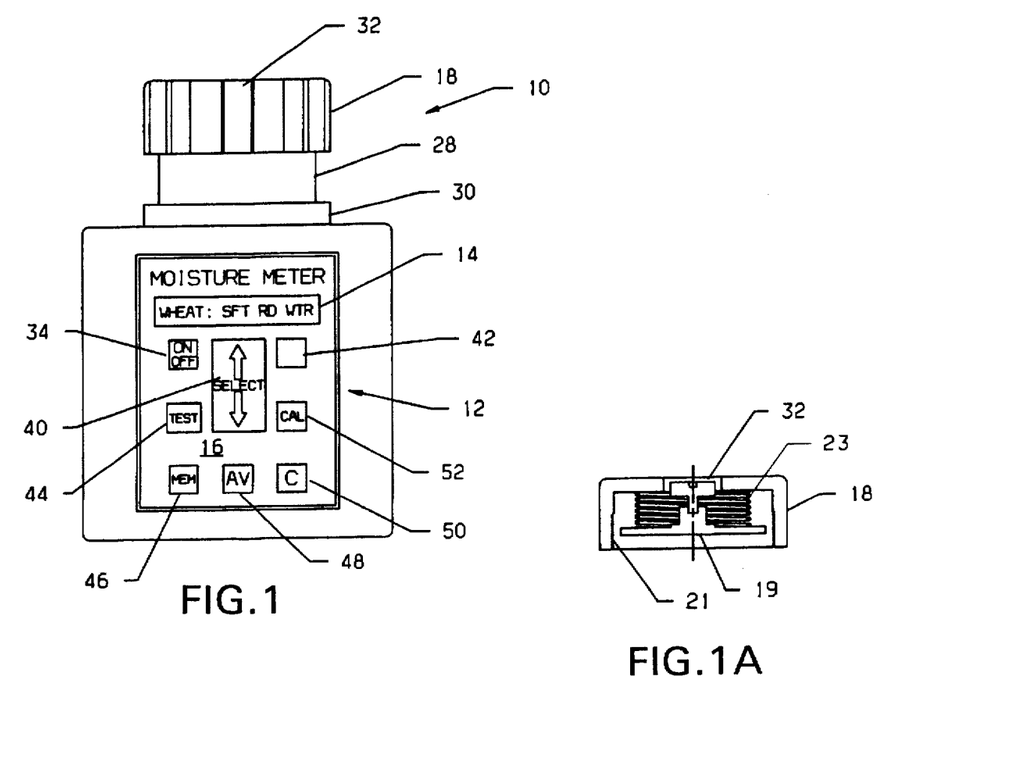
FIG. 1 is a front view of the portable grain moisture meter of the present invention showing the back lighted digital display along with accompanying control buttons.
FIG. 1(A) is a cross sectional view of the cover of the meter of FIG. 1 showing the adjustable grain compression indicating aspects of the cover.
Figure 2:
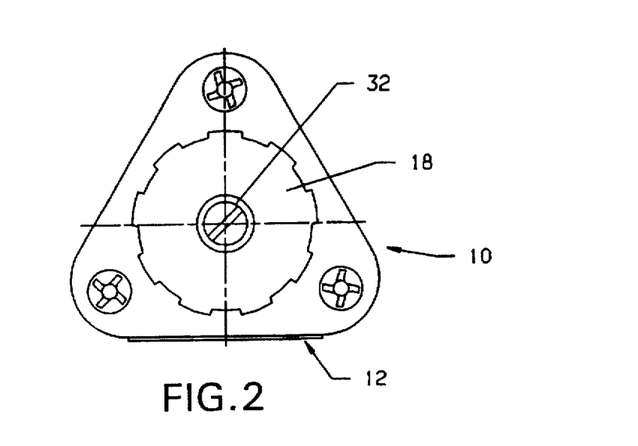
FIG. 2 is a top view of the FIG 1. moisture meter showing the top cap threaded onto the grain compartment of the meter.

With particular reference to FIG. 1(a), it will be seen that the plate (19) is threaded onto a screw (32) found extending through the cap (18) by known complimentary threads on the screw (32) and the plate (19). A spring (23) is located between the plate (19) and the top of the cap (18) with the spring (23) being attached to the top inside surface of the cap (18). The spring (23) is thus able to exert pressure on the grain in the test cell of increasing magnitude as the cap (18) is threaded on to the outside threads (28) of the grain compartment (20). As the cap (18) is thus threaded on, the head of the screw (32) rises within the cap (18) until it is even with the top surface of the cap (18). This easily repeatable orientation of the screw (32) to the cap (18) indicates that the predetermined amount of pressure has been exerted on the grain sample and the test thereof may now proceed. This feature allows the wide variety of grain tested to be tested under easily repeatable conditions of constant pressure allowing an accurate and repeatable constant volume test to be performed.

Once the grain compartment is properly filled with grain and properly compressed, the moisture testing of same may be initiated. The meter (10) is portable and hence battery operated. To power the device, an on/off switch (34) is pressure activated to connect a battery (36) to the electrical circuitry (38) to operate the meter (10) as will be explained later.

With the meter activated, the digital display (14) will display the last grain type tested prior to the present activation. This feature eliminates the need for the meter user to search through a catalog of listed grains for the last grain tested. This feature is made possible by the storage of the last grain tested in the electrically erasable prom (54) known as an EEPROM which retains the signals even after a shutdown of power. If the operator desires to test a grain other than the last grain tested, he must then sequence to the desired grain by using either the up or down arrow switch of a grain select rocker switch (40) until the digital display indicates the desired grain to be tested. The alphabetical list of grains the meter (10) will test is stored in a UVEPROM (55) in alphabetical order and the up and down arrow switches enable the operator to sequence through the grains either forward or backward. Forward sequencing is achieved via the up arrow select switch and the backward sequencing is achieved via the down arrow select switch.

As was mentioned, the electrical circuitry (38) has two distinct types of PROM's due to the differing types of functions performed by the tester. The UVEPROM (55) contains the program instructions and the alphabetic grain list as well as temperature compensation tables for each individual grain. Since these are constants to the device which should not be tampered with by the operator, the data is programmed into the UVPROM (55) at the factory and hence can not be written into by the operator. On the other hand, the EEPROM (54) is used to retain information that may vary during the course of using the tester and is available for the operator to write into. Thus the EEPROM (54) stores the last grain tested, moisture readings taken into memory for averaging, and bias values for each grain inputted by the operator. The EEPROM is able to retain this information even in the absence of power as when the device is turned off or the battery is removed.

Since the various grains to be selected for testing are sometimes quite similar, a detailed full text differentiation is necessary. Such detailing requires a large display and hence the digital display (14) is a 16 character digital display of known manufacture to allow proper grain identification to the operator. Thus as seen in FIG. 1, the display shows WHEAT; SFT RD WTR which utilizes 16 characters when including the two spaces, and thus the device (10) can distinguish other varieties of wheat such as WHEAT; HRD RD WTR; WHEAT; HRD RD SPR; WHEAT; WHITE etc. on the display (14). Prior art devices were eight character devices which could thus display only generic varieties of grain such as WHEAT;RD only without any room remaining to fully detail the wheat variety as being additionally either SFT or HRD and either WTR or SPR.

Since the portable grain moisture meter (10) is sometime used in low light environments such as poorly lit grain stores as well as times of low light such as dawn or dusk, the digital display(14) is back lighted whenever a light switch (42) is actuated. The microprocessor (64) monitors this switch (42) and senses that the switch (42) is pressed. The microprocessor (64) toggles the back light (60) "on" if it was previously "off" and toggles it "off" if it was previously "on". Thus the back light (60) under the microprocessor (64) control can be toggled "off" and "on" at any time that the meter (10) is on. The microprocessor (64) also sends a signal to the 16 character display (14) which produces a solid black dot at a specific character location. This dot remains on as long as the back light (60) is on. This dot acts as a reminder to the operator to turn off the back light (60) in situations where back lighting is unnecessary and where the back lighting may no longer be discernible. This feature saves on the battery life for the meter (10).

When the operator has properly identified the grain he is testing through the grain select switch (40), the test switch (44) is depressed to initiate the capacitance testing of the grain as a dielectric in a known manner. The capacitance testing circuitry (66) of the circuitry (38) completes this testing and displays the moisture content as a percentage by weight on the digital display (14). This measurement may be saved in memory by depressing a memory switch (46). Numerous tests may be thus saved and the average of these tests may be displayed on the digital display (14) as an indicated AVERAGE % moisture by depressing the average switch (48). Clearing the readings from memory is done by depressing the clear switch (50).

The price that grain brings when sold to a storage elevator depends on the grain moisture content being within certain acceptable limits. Thus it may be more profitable to the grain producer to dry the grain to these limits before delivery to the storage silo for sale. Thus it is imperative that the moisture meter being used by the grain producer well correspond to the readings he can expect from the moisture meter at the purchasers silo. This allows the producer to properly prepare his grain for the intended purchaser. This is made possible by the calibration switch (52) of the meter (10). The grain supplier can take his meter (10) to the purchasers station and ask him to check a grain sample that he has already checked. If the purchasers equipment shows either a higher or a lower reading than found with his meter (10) he can re calibrate his meter (10) to match the purchasers equipment. If the purchasers reading from his equipment is +0.3% higher the supplier depresses the calibration switch (52) which displays the amount of bias presently added to the meter (10) for the grain measured. Normally this reading is 0.0% moisture content by weight for all grains. The operator now moves the up arrow of the switch (40) up until a +0.3% bias is displayed on the digital display (14). Henceforth, all the meter (10) readings for the grain previously selected by the supplier on the digital display (14) will be biased up to +0.3% moisture content by weight for all future readings for that particular grain. All other types of grain will not be biased by this preset bias. It should be noted that selecting the calibration switch (52) changed the function of the grain select switch (40) to a bias addition for the last grain selected by the switch (40). If the bias for a particular grain is set to a value other 0.0%, an indicator, namely an asterisk *, is displayed after the moisture reading. Thus a biased reading of 13.5% would be displayed as 13.5%*. The asterisk act as a reminder to the operator that his reading is not unbiased but is adjusted to some remote location as an elevator.

Figure 5:
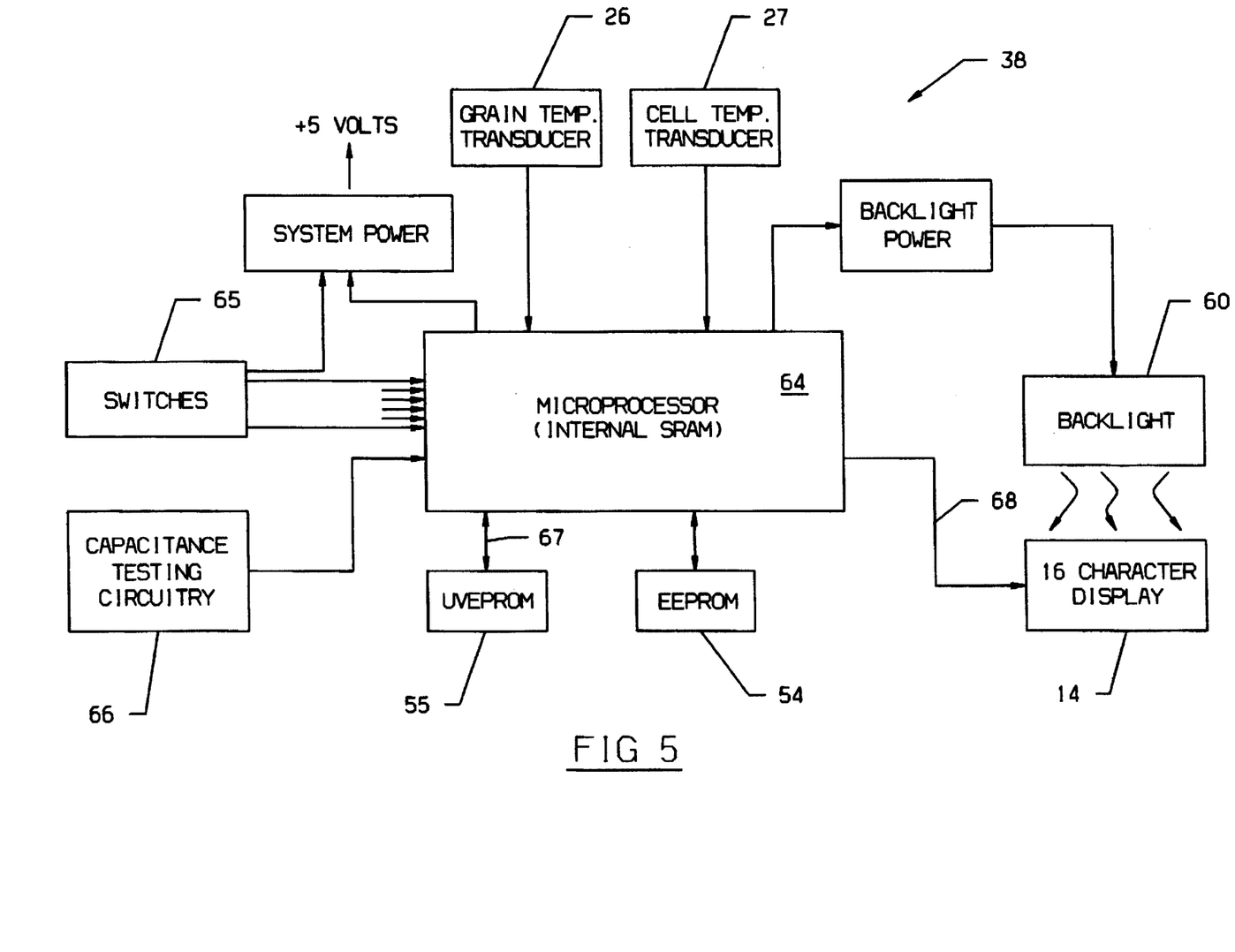
FIG. 5 is a black box electrical schematic of the control circuitry for the moisture meter of the present invention.
Figure 6A:
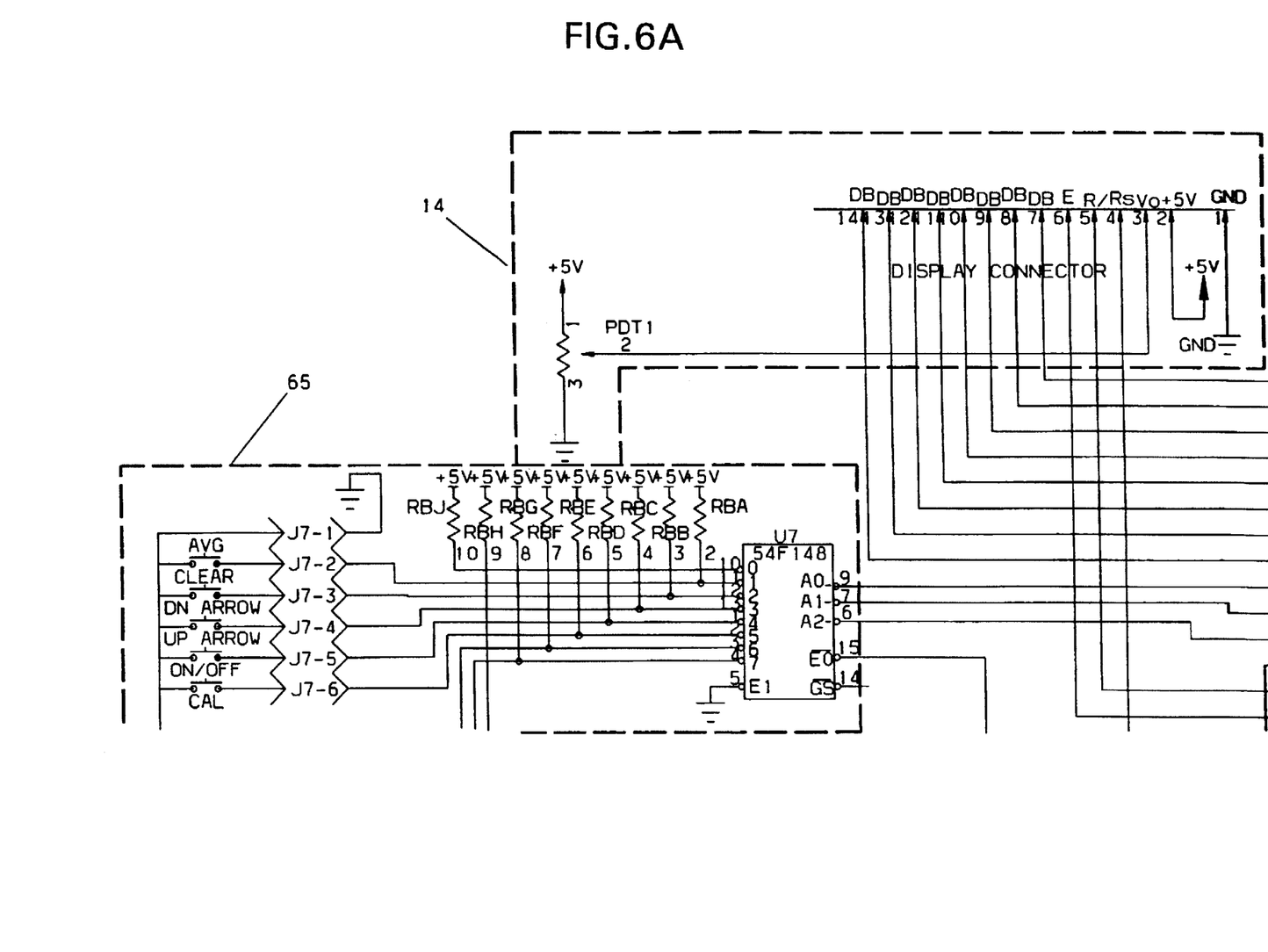
FIG. 6 is a detailed electrical circuit of the FIG. 5 schematic with the black box circuitry detailed therein with dotted lines.
Figure 6B:
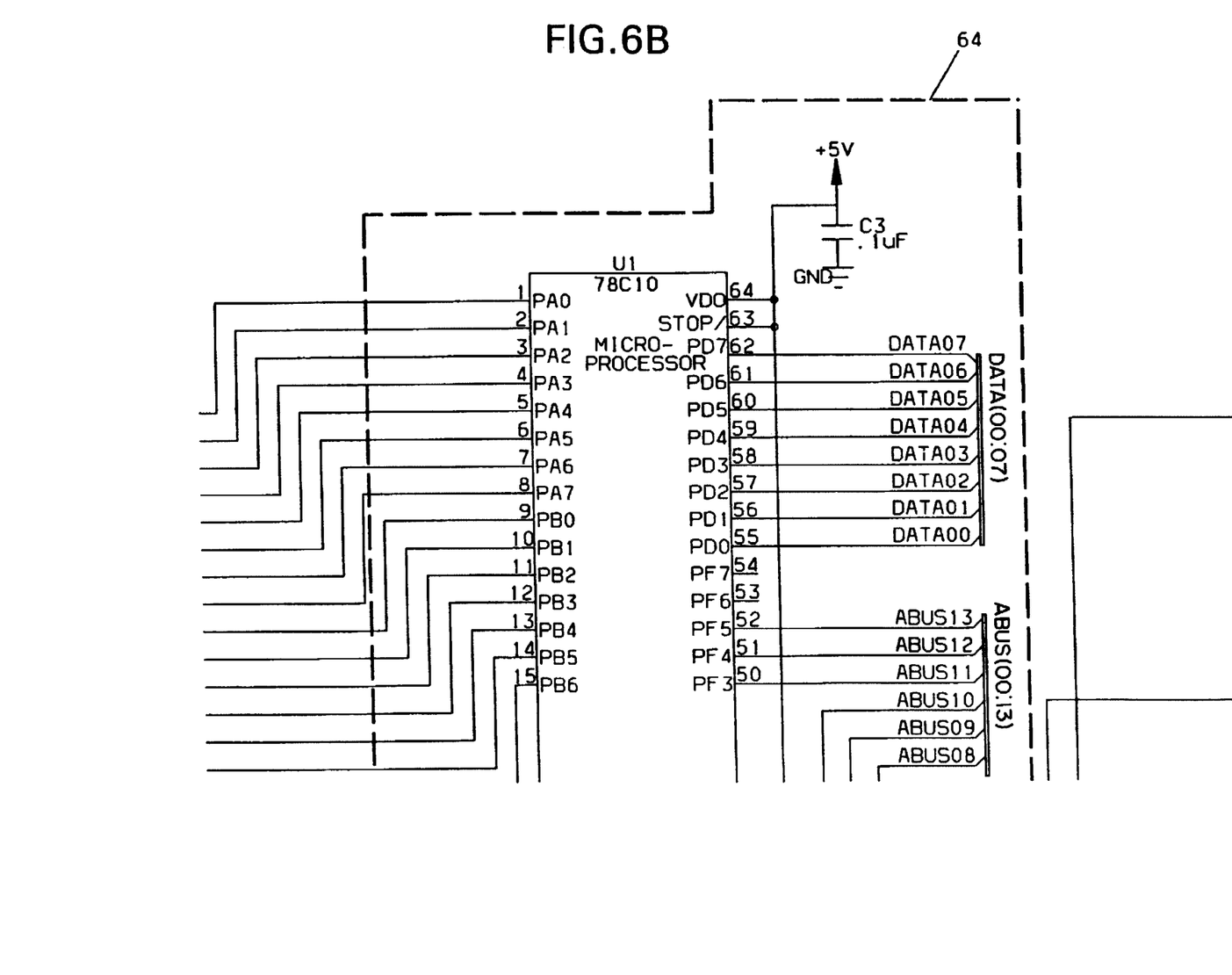
Figure 6C:
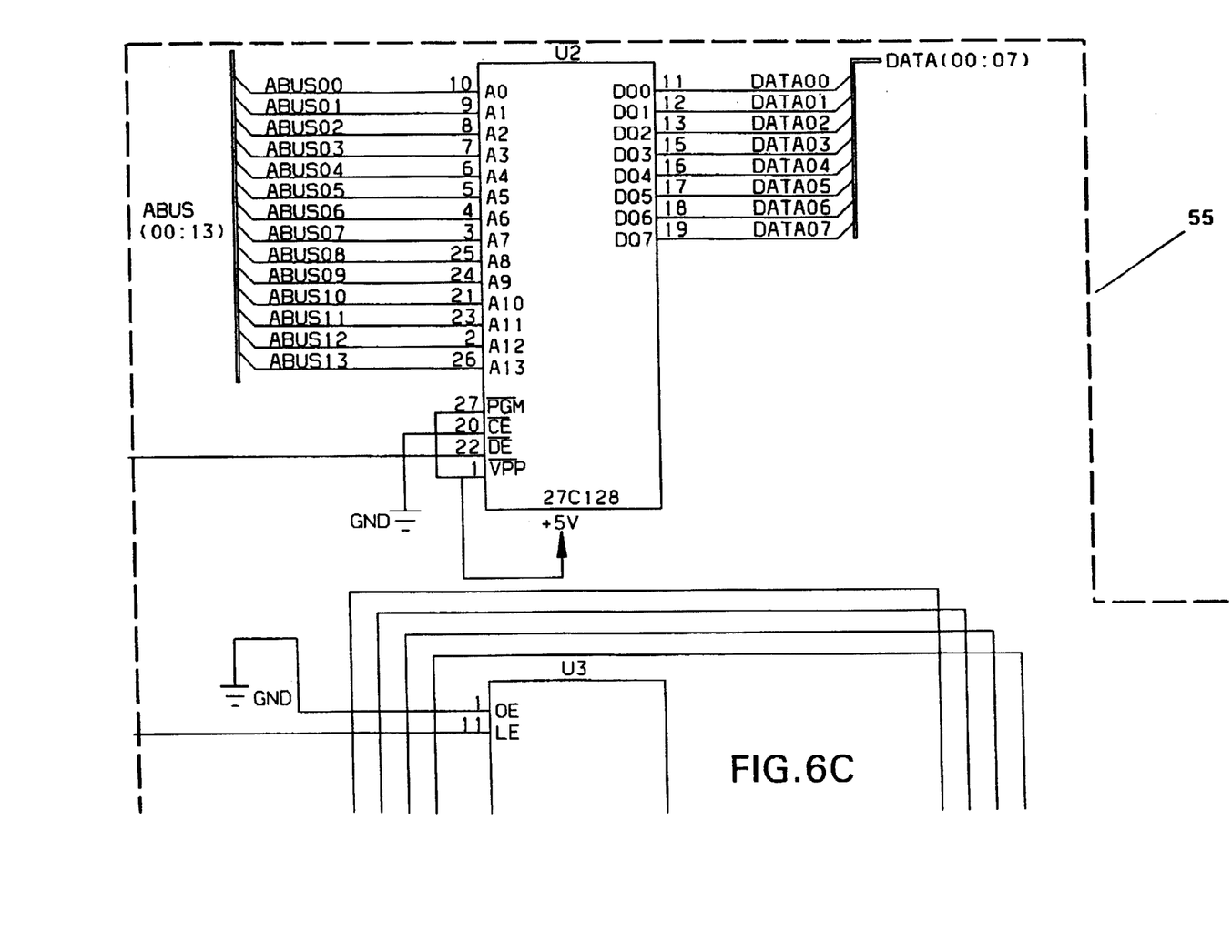
Figure 6D:
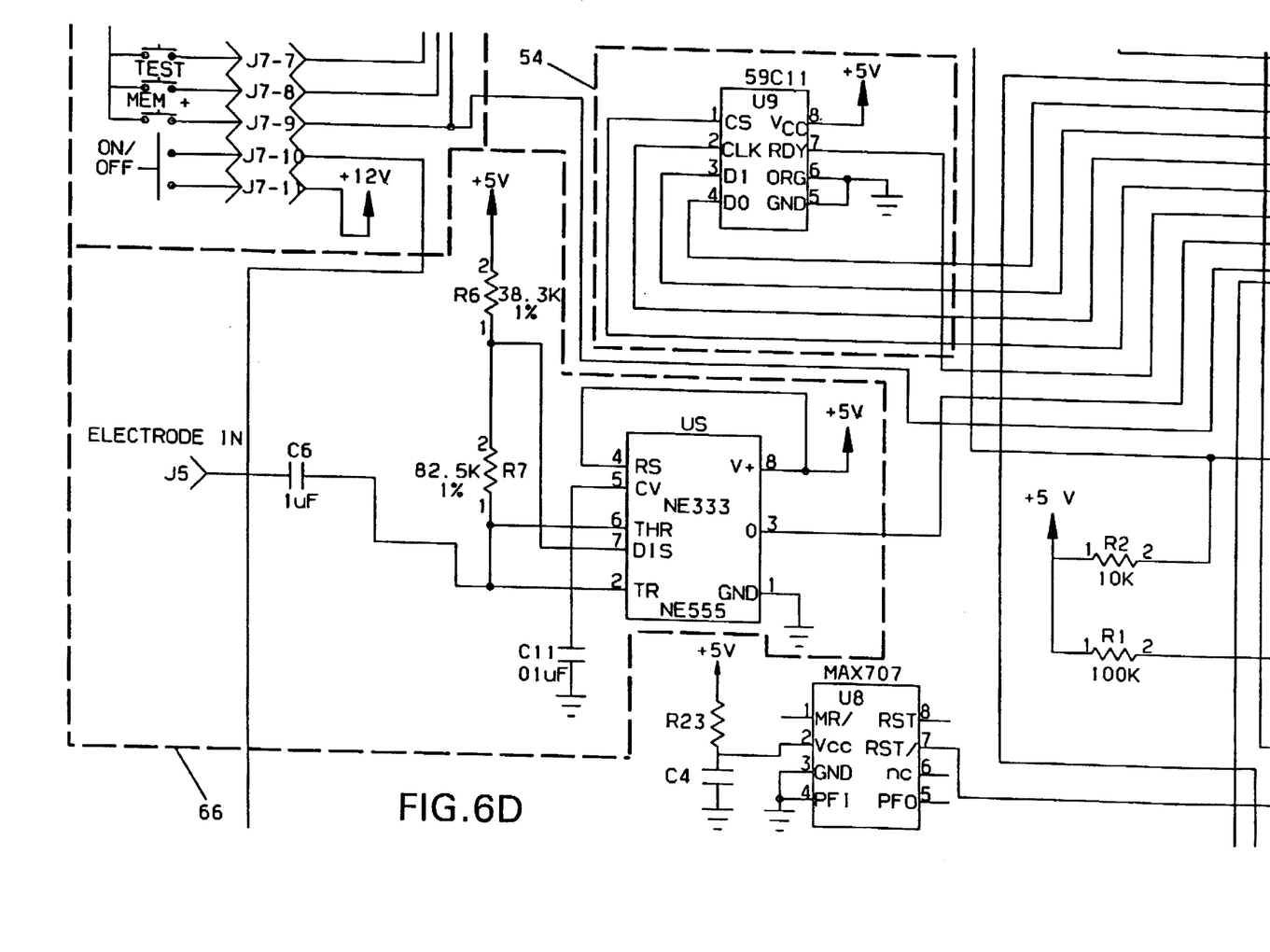
Figure 6E:
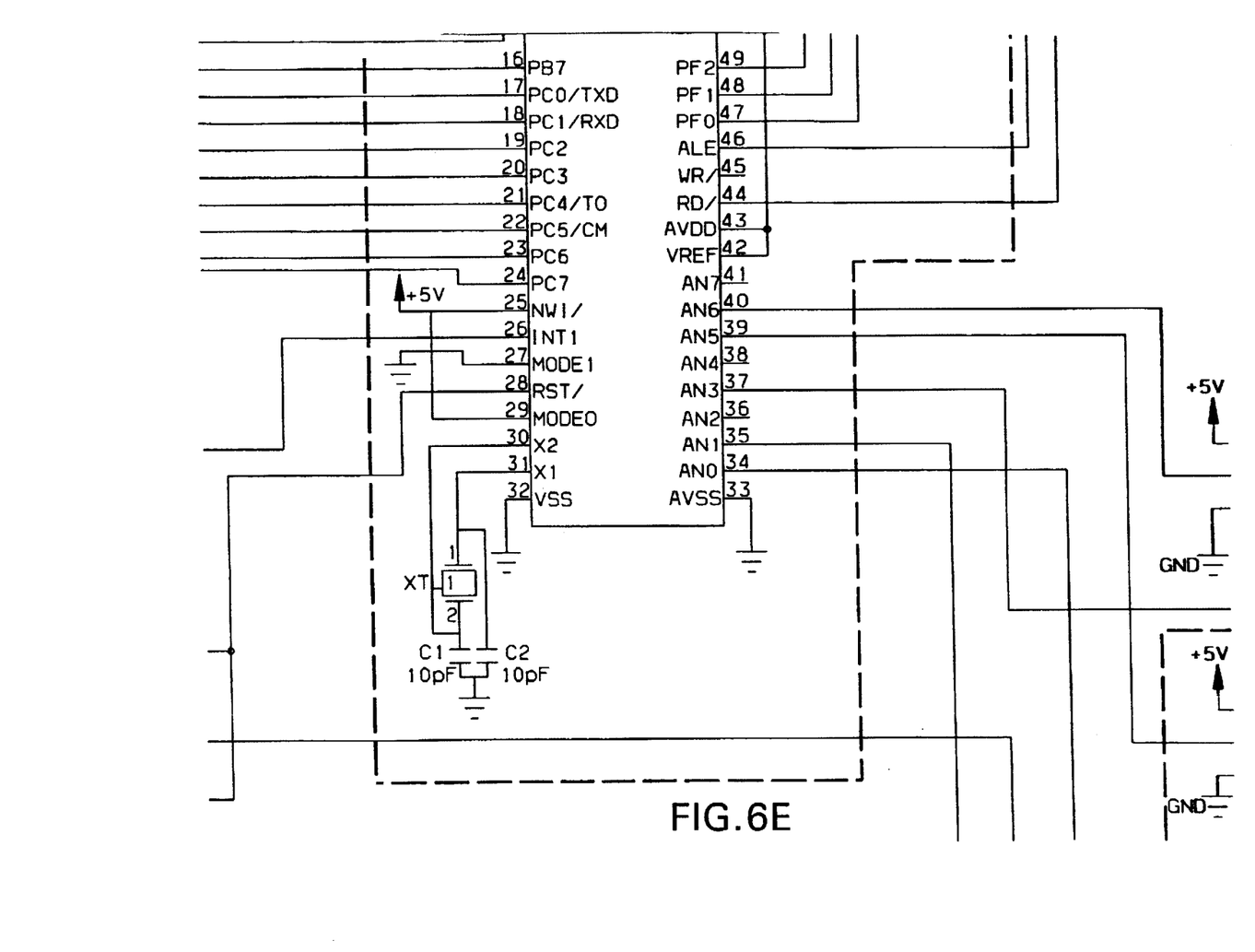
Figure 6F:
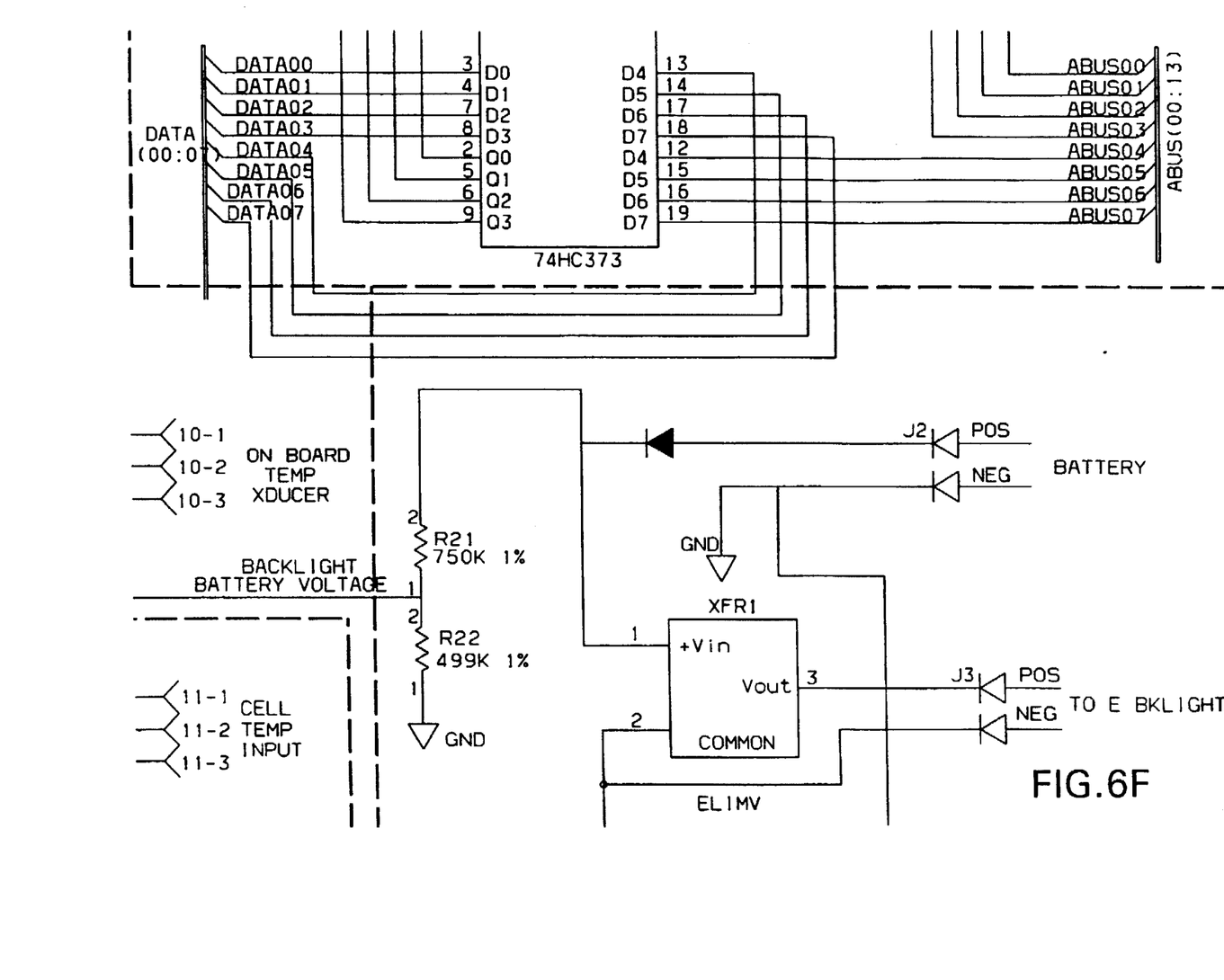
Figure 6G:
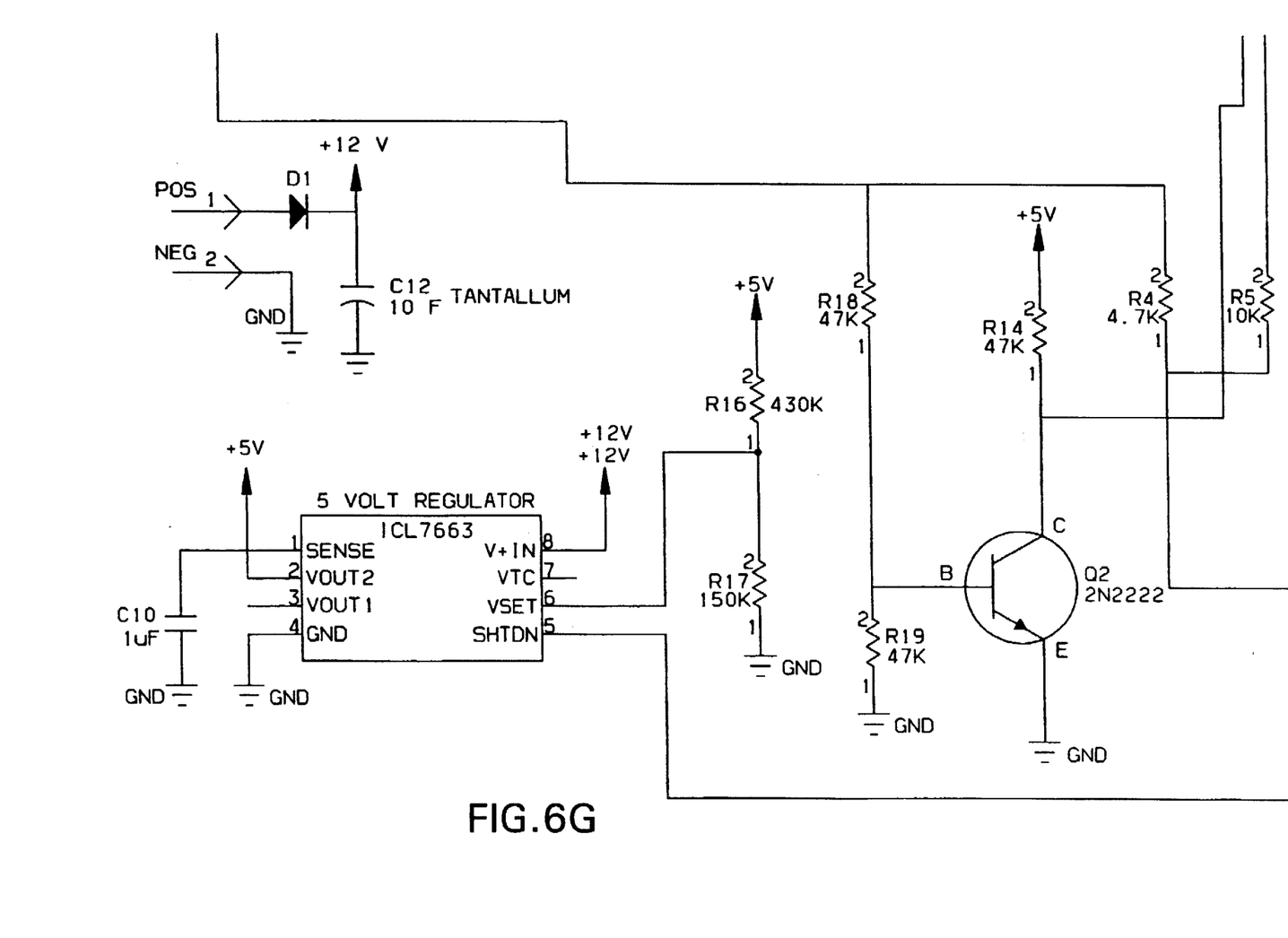
Figure 6H:
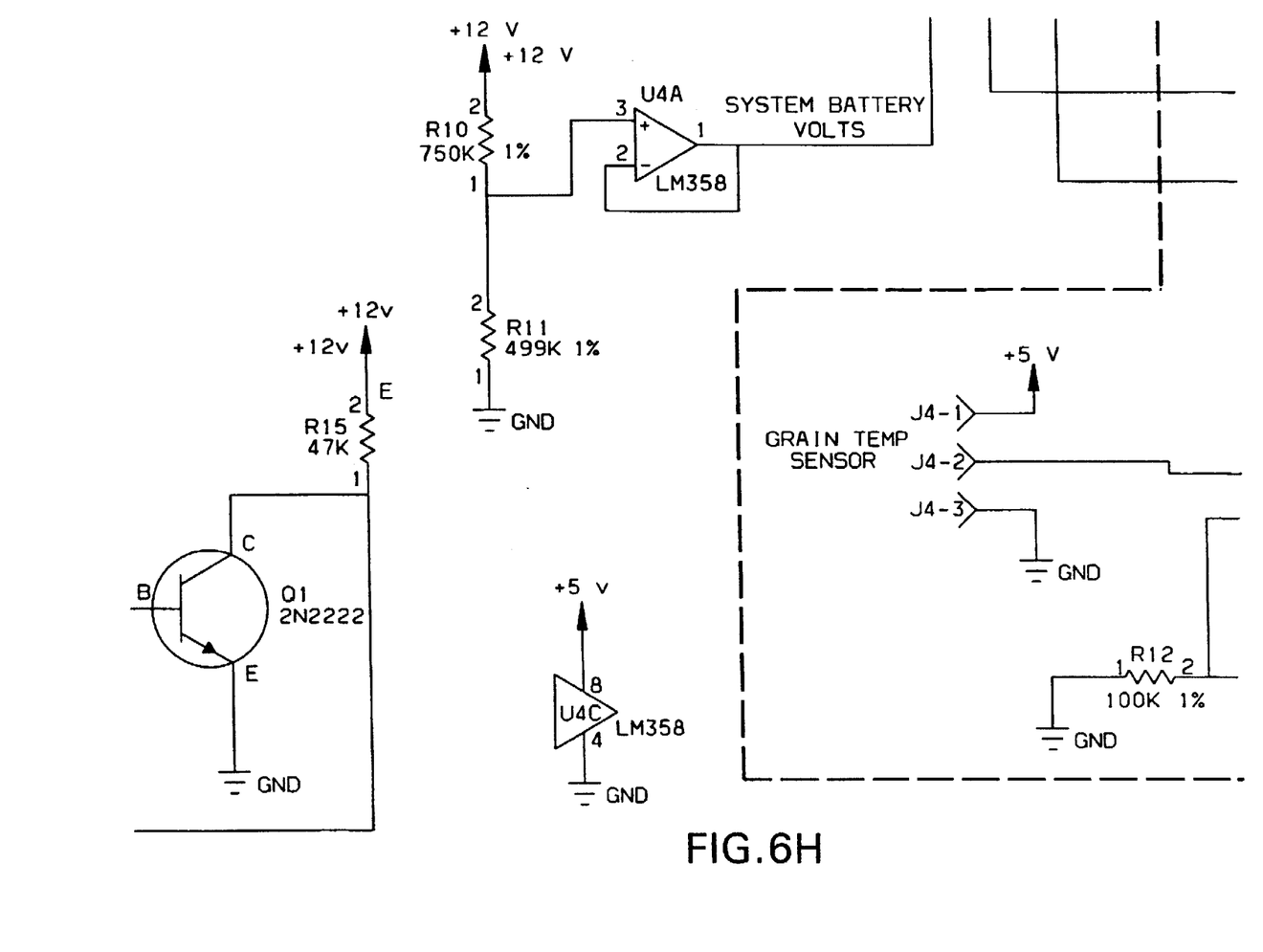
Figure 6J:
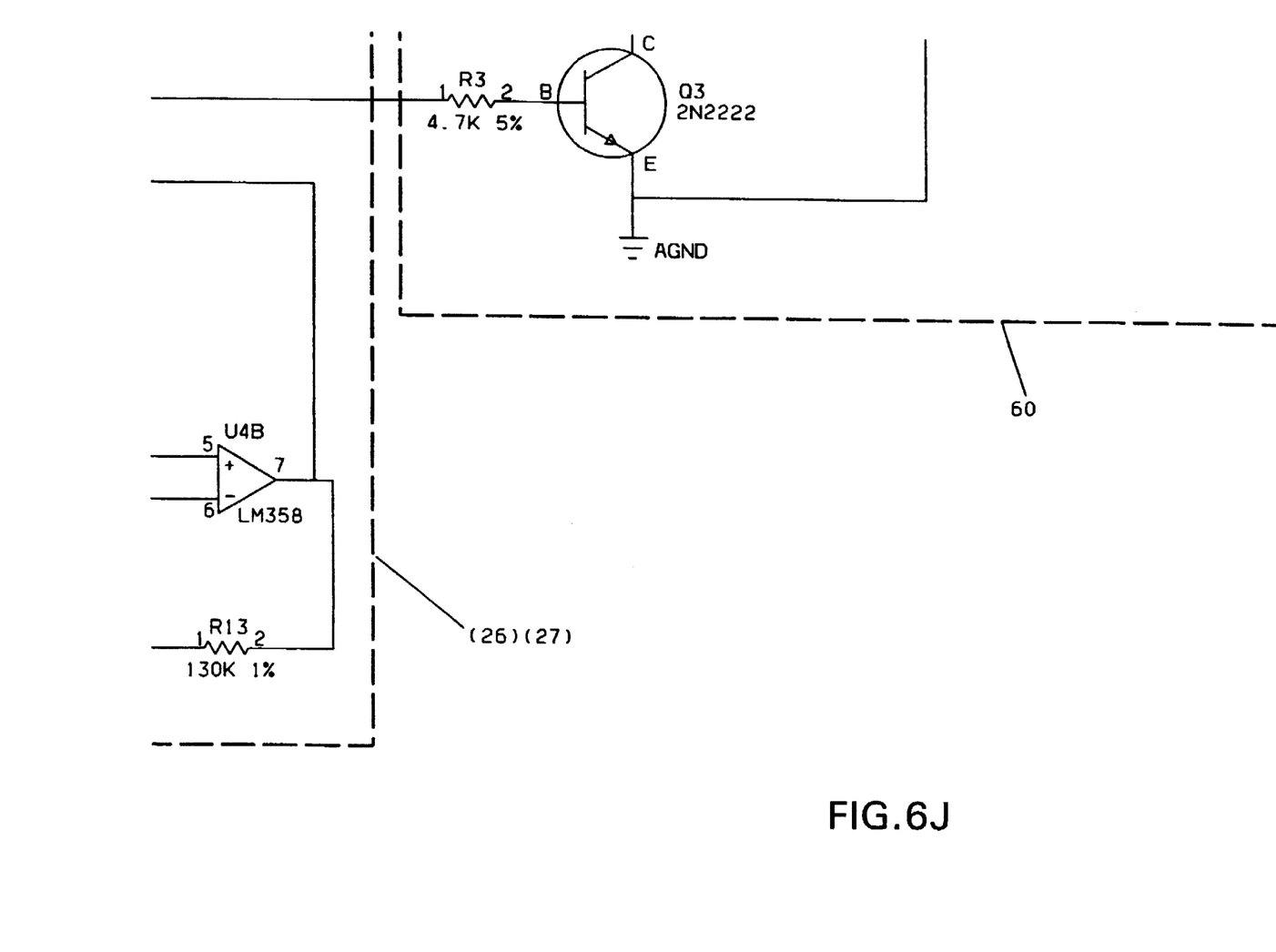

With particular reference to FIGS. 5 and 6, it will be seen that the Switches (44), (46), (48), (50), (52) are generally identified as switches (65) connected to input their signals to the microprocessor (64) which is programmed in a known manner to accomplish the mentioned functions of the various switches (65).

The test switch (44) actuates the microprocessor (64) to initiate a known capacitance type moisture test system (66) discussed earlier. The data from the system (66) is then correlated with the grain type selected from the UVPROM (55) and the grain moisture is displayed on the display (14) along bus (68). Should one want this reading to be saved, the switch (46) tells the microprocessor (64) to store the data in EEPROM (54) at a first data location. Subsequent measurements may similarly be made and stored. Depressing the average button (48) will execute a calculation program in the microprocessor (64) to access all the test readings stored in the prom (54) and to divide by the number of such test readings to calculate an average which is then displayed along bus (68) to the display (14). Depressing the switch (50) will command the microprocessor (64) to clear the test data stored in the EEPROM (54).

The switch (52) allows the microprocessor (64) to bypass the alphabetical grain catalogue stored in UVPROM (55) and allow the switch (40) to act as a simple up/down counter along line (68) to either add or subtract increments of moisture measurement received from the system (66) by the microprocessor (64) for displaying in the 16 character display (14). Initially, the amount of incremental bias is displayed on the display (14) as the switch (40) is moved up or down to the desired incremental data. This data is associated with the last grain type chosen by switch (40) and subsequent tests for this grain actuated by switch (44) will display the moisture content on display (14) having this bias built in along with an asterisk notation as was mentioned.

The accuracy of the grain measurement is assured by two temperature transducers (26) and (27) which measure both the grain temperature as well as the grain compartment (20) temperature (test cell temperature). The test cell acts as a thermal heat sink to the grain and the grain temperature will tend to slowly drift toward equilibrium with the test cell. Thus the measurement of the grain temperature by itself is erroneous. Both of the temperature transducers are inputted into the microprocessor (64) which mathematically calculates a differential temperature based on both of these temperature readings. This differential temperature measurement assures a grain temperature reading that is more accurate than what could be achieved via a single temperature measurement.

To accomplish the above, the microprocessor (64) reads the frequency of the capacitance test circuit (66) and then obtains the moisture reading based on the grain frequency-to-moisture tables stored in the UVPROM (55) whenever a moisture test is initiated by depressing the switch (44). Each grain has its own frequency-to-moisture tables stored in the UVPROM (55) which the microprocessor accesses along bus (65). The microprocessor (64) then calculates the differential temperature of the grain temperature transducer (26) and the cell temperature transducer (27), and adds or subtracts from the moisture reading depending on the grain selected and the differential temperature measured. Temperature compensation tables are also stored in the UVPROM (55) and each grain has its own table. By using this technique, the meter(10) is able to implement automatic temperature compensation for each grain based on the grain type and the differential temperature measured for the grain and the test cell.

Certain modifications and additions have been deleted herein for the sake of conciseness and readability. As an example details of the construction and operation of well known circuit elements are deleted. However, all such are intended to be included in the scope and understanding of the following claims.

What is claimed is:

1. A temperature compensation assembly for a grain moisture meter comprising:

a test cell for holding grain to be tested therein;

grain moisture measuring means for determining the moisture content of grain in said test cell;

first temperature measuring means for measuring the temperature of the grain;

second temperature measuring means for measuring the temperature of said test cell; and computer means for calculating a temperature compensation factor for compensating said moisture measuring means based on the differential of the temperature sensed by said first and second temperature measuring means.

2. A temperature compensation assembly as set forth in claim 1 wherein said computer means includes a microprocessor connected to said first and second temperature measuring means to calculate a differential between signals supplied therefrom.

3. A temperature compensation assembly as set forth in claim 2 including an EPROM connected to said microprocessor and having a look up table of empirically derived temperature compensation factors for various temperature differentials calculated by said microprocessor and accessible by said microprocessor for modifying the measurement of said moisture measuring means.

4. A temperature compensating assembly for a grain moisture meter comprising:

grain holding means;

moisture measuring means for testing the moisture of the grain in said holding means;

temperature measuring means for determining the grain temperature of the grain being tested;

a main body enclosing said grain holding means and having electronic circuitry therein for calculating grain moisture and for displaying the grain tested in a full text digital display;

a test cell formed in said grain holding means for holding a predetermined volume of grain therein;

threaded cover means for exerting pressure on the grain within said test cell in response to the threading of said cover means on said test cell; and indicating means for providing an indication of predetermined pressure being exerted on the grain in said test cell.

5. A temperature assembly as set forth in claim 4 wherein said cover means includes a threaded cap and comprises a screw movably extending through said cap in response to the threading of said cap on said test cell.

6. A temperature assembly as set forth in claim 5 wherein said predetermined pressure is indicated by having screw extend to a top surface of said cap.

7. A temperature assembly said as set forth in claim 4 wherein said digital display is a 16 character digital display.

8. A temperature assembly as set forth in claim 7 including a back light selectively actuated to illuminate said 16 character display.

9. A temperature assembly as set forth in claim 8 including an indicator on said 16 character display for indicating that said back light is "on".

10. A temperature assembly as set forth in claim 9 wherein said indicator is a black dot formed as one character of said 16 character digital display along with the digital display.

11. A temperature assembly as set forth in claim 10 including a computer means having a PROM having an alphabetical listing of the grains the meter is capable of listing and a microprocessor connected to said PROM and said 16 character display to display the alphabetical listing of gains in response to a switch signal.

12. A temperature assembly as set forth in claim 11 including a two position switch connected to said microprocessor for having the microprocessor sequentially scroll the alphabetical grain listing forward in a first switch position and backwards in a second switch position.

13. A temperature assembly as set forth in claim 12 including computer means for individually displaying on said 16 character display a series of grains in full text from a memory stored listing of grains that the moisture meter is capable of testing and bias means for biasing the signal established by said electronic circuitry to calibrate the meter to a remotely located meter.

14. A temperature assembly as set forth in claim 13 including a microprocessor connected to said 16 character digital display and a capacitance circuit means and wherein said bias means includes a digital counter within said microprocessor for adding an incremental amount to the signal received by the microprocessor from said capacitance circuit means in response to a switch signal.

15. A temperature assembly as set forth in claim 14 including a two position switch connected to said microprocessor establishing a first signal to said microprocessor to add an incremental amount to the signal from said capacitance circuit means and a second signal to add a negative incremental amount.

16. A temperature assembly as set forth in claim 15 wherein said 16 character display displays the signal established by said capacitance circuit means as modified by said bias means in response to a "TEST" switch signal.

17. A temperature assembly as set forth in claim 16 wherein said microprocessor sends a signal to said 16 character display to display an asterisk as one character of said display whenever said bias means is activated to indicate that the signal of the capacitance circuit means has been biased by said bias means.

18. A temperature assembly as set forth in claim 16 wherein the incrementally added amount of said bias means along with the signal of the capacitance circuit means is stored by said microprocessor in an EPROM to allow this data to be recovered after a shut down of the meter or a power failure.

* * * * *